(12) United States Patent
Reich et al.

(10) Patent No.: US 8,623,946 B2
(45) Date of Patent: Jan. 7, 2014

(54) STABILIZATION OF BODY-CARE AND HOUSEHOLD PRODUCTS

(75) Inventors: Oliver Reich, Limburgerhof (DE); Michael Schork, Riehen (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/000,370

(22) PCT Filed: Jun. 19, 2009

(86) PCT No.: PCT/EP2009/057661
§ 371 (c)(1),
(2), (4) Date: Jan. 28, 2011

(87) PCT Pub. No.: WO2009/156340
PCT Pub. Date: Dec. 30, 2009

(65) Prior Publication Data
US 2011/0123464 A1    May 26, 2011

(30) Foreign Application Priority Data
Jun. 27, 2008  (EP) .................................... 08159256

(51) Int. Cl.
*A61K 8/49*  (2006.01)
*A61K 47/22*  (2006.01)
*A61Q 11/00*  (2006.01)
*C07D 307/80*  (2006.01)
*A61Q 3/02*  (2006.01)
*A61Q 17/04*  (2006.01)

(52) U.S. Cl.
USPC ........................... 524/111; 549/302; 424/400

(58) Field of Classification Search
USPC ....................................................... 524/111
See application file for complete search history.

(56) References Cited

U.S. PATENT DOCUMENTS

| 2003/0109611 A1 | 6/2003 | Schrinner et al. |
| 2006/0052491 A1 | 3/2006 | Braig et al. |
| 2009/0258041 A1 | 10/2009 | Mongiat et al. |

FOREIGN PATENT DOCUMENTS

| EP | 1291384 A | 3/2003 |
| EP | 0308084 A | 5/2003 |
| WO | 0025731 A | 5/2000 |
| WO | 2007048645 A | 5/2007 |

*Primary Examiner* — Walter Webb
(74) *Attorney, Agent, or Firm* — Shiela A. Loggins

(57) ABSTRACT

Described is the use of specific lactone compounds for protecting body-care and household products from photolytic and oxidative degradation. These compounds perform outstanding antioxidant properties.

15 Claims, No Drawings

STABILIZATION OF BODY-CARE AND HOUSEHOLD PRODUCTS

The present invention relates to the use of selected lactone compounds as stabilizers for protecting body-care and household products from photolytic and oxidative degradation.

The product trend of recent years towards increasing use of natural substances based on oil and fat in cosmetic formulations and household products also increases the problem of the oxidative degradation of fats and oils, resulting in rancidity. Natural oils or unsaturated fatty acids are hardly ever absent from emulsions. Oxidative changes may sometimes produce reactive metabolites, for example ketones, aldehydes, acids, epoxides and lipoperoxides.

As a result there is on the one hand an undesirable change in the smell of the products and on the other hand substances may be obtained which may alter the skin tolerance. The uncontrolled formation of free radicals on the skin contributes primarily to the initiation and progression of a multitude of pathophysical modulations, for example inflammation, cancerogenesis and the like.

However, oxidative degradation processes are not only found in the case of natural substances based on oil and fat. They are also found in a number of other cosmetic ingredients, such as fragrances and odoriferous substances, vitamins, colourants and the like.

To prevent oxidative degradation processes (photooxidation, autooxidation), so-called anti-oxidants (AO) are therefore used in cosmetic and food products. These antioxidants may be classified into compounds which prevent oxidation (complex formers, reducing agents and the like) and into compounds which interrupt the free radical chain reactions, for example butylated hydroxytoluene (BHT), butylated hydroxyanisol (BHA), gallates, such as propyl-gallate (PG), or t-butylhydroquinone (TBHQ). However, the latter compounds often do not meet the requirements with respect to pH stability as well as to light and temperature stability.

As a consequence the actives in such containers unadvantageously change their properties due to autoxidative processes. This results for example in a reduction of viscosity and changes in color or smell.

Furthermore, the growing product trend in the recent years has also resulted in an increased use of transparent (glass, PET etc.) containers for cosmetic formulations and household products. Although both glass and ordinary plastics have a certain inherent absorption in the UV-B-range the absorption in the UV-A range is very low.

Various stabilization techniques for clear package products by UV absorption are commonly used and well known. For example broad-band UV light stabilizers of the benzotriazole class enhance product stability and shelf live due to their very good UV-A and UV-B absorption properties compared to other absorbers such as benzophenones which mainly absorb UV-B. The most effective today known stabilizers for preventing or delaying light induced fading of transparent packaged products are e.g. benzotriazole derivatives known under the trade names Ciba TINOGARD HS or Ciba TINOGARD TL.

Surprisingly, it has been found that specific stabilizers based on lactone derivatives perform stabilizer properties and are therefore suitable for product protection.

Therefore, the present invention relates to the use of stabilizers of formula

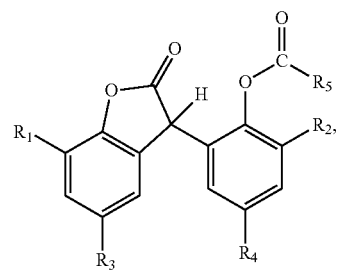

(1)

wherein $R_1$ and $R_2$ are each independently of one another hydrogen; or $C_1$-$C_8$alkyl;

$R_3$ and $R_4$ are each independently of one another $C_1$-$C_{12}$alkyl; and $R_5$ is $C_1$-$C_7$alkyl;

for protecting body-care and household products from photolytic and oxidative degradation.

Alkyl having up to 12 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl (tert-octyl), 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl or dodecyl. One of the preferred definitions for $R_1$ and $R_2$ is, for example, $C_1$-$C_6$alkyl, especially $C_1$-$C_4$alkyl, e.g. tert-butyl. Preferably, $R_3$ and $R_4$ are $C_4$-$C_{12}$alkyl, especially $C_4$-$C_{10}$alkyl, e.g. $C_8$alkyl. A preferred definition of $R_5$ is $C_1$-$C_4$alkyl, especially $C_1$-$C_3$alkyl, e.g. methyl.

Preferably compounds of formula (1) are used, wherein $R_1$ and $R_2$ are each independently of one another hydrogen; or $C_1$-$C_4$alkyl;

$R_3$ and $R_4$ are each independently of one another $C_4$-$C_{10}$alkyl, and $R_5$ is $C_1$-$C_4$alkyl.

Further preferred compounds of the formula (1) are those wherein $R_3$ and $R_4$ are tert-octyl.

Of special interest is the compound of the formula (1) wherein $R_1$ and $R_2$ are hydrogen, $R_3$ and $R_4$ are tert-octyl, and $R_5$ is methyl.

The preparation of the compounds of the formula I is for example disclosed in EP-A-0 871 066.

The stabilizers of formula (1) can be used together with UV absorbers as listed in Tables 1-3, phenolic or non-phenolic antioxidants, with complex formers or merocyanine derivatives are particularly suitable for protecting body-care and household products against photolytic degradation.

Examples of organic UV filters that can be used in admixture with the compounds of formula (1) are listed in the following Tables 1 to 3:

TABLE 1

Suitable UV filter substances which can be additionally used with the compounds of formula (1)

p-aminobenzoic acid derivatives, for example 4-dimethylaminobenzoic acid 2-ethylhexyl ester;
salicylic acid derivatives, for example salicylic acid 2-ethylhexyl ester;
benzophenone derivatives, for example 2-hydroxy-4-methoxybenzophenone and its 5-sulfonic acid derivative;
diphenylacrylates, for example 2-ethylhexyl 2-cyano-3,3-diphenylacrylate, and 3-(benzofuranyl) 2-cyanoacrylate;
3-imidazol-4-ylacrylic acid and esters;
benzofuran derivatives, especially 2-(p-aminophenyl)benzofuran derivatives, described in EP-A-582 189, U.S. Pat. No. 5,338,539, U.S. Pat. No. 5,518,713 and EP-A-613 893;
polymeric UV absorbers, for example the benzylidene malonate derivatives described in EP-A-709 080;
camphor derivatives, for example 3-(4'-methyl)benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylenedimethine)-bis(7,7-dimethyl-2-oxo-bicyclo[2.2.1]heptane-1-methanesulfonic acid) and salts, 3-(4'-sulfo)benzylidene-bornan-2-one and salts; camphorbenzalkonium methosulfate;
hydroxyphenyltriazine compounds, for example 2-(4'-methoxyphenyl)-4,6-bis(2'-hydroxy-4'-n-octyloxyphenyl)-1,3,5-triazine; 2,4-bis{[4-(3-(2-propyloxy)-2-hydroxy-propyloxy)-2-hydroxy]-phenyl}-6-(4-methoxyphenyl)-1,3,5-triazine; 2,4-bis{[4-(2-ethyl-hexyloxy)-2-hydroxy]-phenyl}-6-[4-(2-methoxyethyl-carboxyl)-phenylamino]-1,3,5-triazine; 2,4-bis{[4-(tris-(trimethylsilyloxy-silylpropyloxy)-2-hydroxy]-phenyl}-6-(4-methoxyphenyl)-1,3,5-triazine; 2,4-bis{[4-(2''-methylpropenyloxy)-2-hydroxy]-phenyl}-6-(4-methoxyphenyl)-1,3,5-triazine; 2,4-bis{[4-(1',1',1',3',5',5',5'-heptamethyltrisilyl-2''-methyl-propyloxy)-2-hydroxy]-phenyl}-6-(4-methoxyphenyl)-1,3,5-triazine; 2,4-bis{[4-(3-(2-propyloxy)-2-hydroxy-propyloxy)-2-hydroxy]-phenyl}-6-[4-ethylcarboxy)-phenylamino]-1,3,5-triazine;
benzotriazole compounds, for example 2,2'-methylene-bis(6-(2H-benzotriazol-2-yl)-4-(1,1,3,3-tetramethylbutyl)-phenol;
trianilino-s-triazine derivatives, for example 2,4,6-trianiline-(p-carbo-2'-ethyl-1'-oxy)-1,3,5-triazine and the UV absorbers disclosed in U.S. Pat. No. 5,332,568, EP-A-517 104, EP-A-507 691, WO 93/17002 and EP-A-570 838;
2-phenylbenzimidazole-5-sulfonic acid and salts thereof;
menthyl o-aminobenzoates;
physical sunscreens coated or not as titanium dioxide, zinc oxide, iron oxides, mica, MnO, $Fe_2O_3$, $Ce_2O_3$, $Al_2O_3$, $ZrO_2$. (surface coatings: polymethylmethacrylate, methicone (methylhydrogenpolysiloxane as described in CAS 9004-73-3), dimethicone, isopropyl titanium triisostearate (as described in CAS 61417-49-0), metal soaps as magnesium stearate (as described in CAS 4086-70-8), perfluoroalcohol phosphate as C9-15 fluoroalcohol phosphate (as described in CAS 74499-44-8; JP 5-86984, JP 4-330007)).
The primary particle size is an average of 15 nm-35 nm and the particle size in dispersion is in the range of 100 nm-300 nm.
aminohydroxy-benzophenone derivatives disclosed in DE 10011317, EP 1133980 and EP 1046391
phenyl-benzimidazole derivatives as disclosed in EP 1167358
the UV absorbers described in "Sunscreens", Eds. N. J. Lowe, N. A. Shaath, Marcel Dekker, Inc., New York and Basle or in Cosmetics & Toiletries (107), 50ff (1992) also can be used as additional UV protective substances.

TABLE 2

Suitable UV filter substances which can be additionally used with the UV absorbers according to the present invention

| | |
|---|---|
| DE 10013318 | T 1 pp 8-9, all Examples pp 10-13, T 2 pp 13-14, all Examples p 14, Ex A, B, C, D, E, F pp 19-20 |
| DE102004038485A1 | Formula 1 on p 2; Ex 1-4 on p 13; |
| DE102004039281A1 | Formulas I-II on p 1; Ex Ia-Iae on pp 7-12; Ex IIa-IIm on pp 14-15; Ex 1-25 on pp 42-56; |
| DE 10206562 A1 | Ex 1-3 p 10, Ex 4-7 p 11, Ex 8-15 pp 12-14 |
| DE 10238144 A1 | Ex on p 3-5; |
| DE 10331804 | T 1 p 4, T 2 + 3 p 5 |
| DE 19704990 A1 | Ex 1-2 on pp 6-7; |
| EP 613 893 | Ex 1-5 + 15, T 1, pp 6-8 |
| EP 0 998 900 A1 | Ex on pp 4-11 |
| EP 1 000 950 | Comp. In Table 1, pp 18-21 |
| EP 1 005 855 | T 3, p 13 |
| EP 1 008 586 | Ex 1-3, pp 13-15 |
| EP 1 008 593 | Ex 1-8, pp 4-5 |
| EP 1 027 883 | Compound VII, p 3 |
| EP 1 027 883 | Comp I-VI, p 3 |
| EP 1 028 120 | Ex 1-5, pp 5-13 |
| EP 1 059 082 | Ex 1; T 1, pp 9-11 |
| EP 1 060 734 | T 1-3, pp 11-14 |
| EP 1 064 922 | Compounds 1-34, pp 6-14 |

TABLE 2-continued

Suitable UV filter substances which can be additionally used with the UV absorbers according to the present invention

| | |
|---|---|
| EP 1 077 246 A2 | Ex 1-16 on pp 5-11; |
| EP 1 081 140 | Ex 1-9, pp 11-16 |
| EP 1 103 549 | Compounds 1-76, pp 39-51 |
| EP 1 108 712 | 4,5-Dimorpholino-3-hydroxypyridazine |
| EP 1 123 934 | T 3, p 10 |
| EP 1 129 695 | Ex 1-7, pp 13-14 |
| EP 1 167 359 | Ex 1, p 11 and Ex 2, p 12 |
| EP 1 232 148 B1 | Ex 4-17 on pp 3-5; |
| EP 1 258 481 | Ex 1, pp 7, 8 |
| EP 1 310 492 A1 | Ex 1-16 on pp 22-30 |
| EP 1 371 654 A1 | Ex on pp 5-7 |
| EP 1 380 583 A2 | Ex 1, p 6; |
| EP 1 423 351 A2 | Ex 1-16 on pp 31-37; |
| EP 1 423 371 A1 | T 1 on pp 4-8, Ex on p 9, Ex 1-9 on pp 36-42; |
| EP 1 454 896 A1 | Ex 1-5 on pp 10-13, Examples on pp 4-5; |
| EP 1 471 059 A1 | Ex 1-5 on pp 4-5; |
| EP 1 484051 A2 | Formula III-VII on pp18-19, Ex 7-14 on pp 7-9, Ex 18-23 on pp 11-12, Ex 24-40 on pp 14-17; |
| EP 1648849 A2 | Formula 1 on p 4; Ex 1-2 on pp 13-17; Ex C10 and O10 on pp15-16; |
| EP 420 707 B1 | Ex 3, p 13 (CAS Reg. No 80142-49-0) |
| EP 503 338 | T 1, pp 9-10 |
| EP 517 103 | Ex 3, 4, 9, 10 pp 6-7 |
| EP 517 104 | Ex 1, T 1, pp 4-5; Ex 8, T 2, pp 6-8 |
| EP 626 950 | all compounds |
| EP 669 323 | Ex 1-3, p 5 |
| EP 743 309 A1 | Ex 1-12 on pp 18-24; |
| EP 780 382 | Ex 1-11, pp 5-7 |
| EP 823 418 | Ex 1-4, pp 7-8 |
| EP 826 361 | T 1, pp 5-6 |
| EP 832 641 | Ex 5 + 6 p 7; T 2, p 8 |
| EP 832 642 | Ex 22, T 3, pp 10-15; T 4, p 16 |
| EP 848944 A2 | Formulas I and II on p 1; Ex on p 8; Examples on p 10; |
| EP 852 137 | T 2, pp 41-46 |
| EP 858 318 | T 1, p 6 |
| EP 863 145 | Ex 1-11, pp 12-18 |
| EP 878 469 A1 | T 1, pp 5-7; |
| EP 895 776 | Comp. In rows 48-58, p 3; R 25 + 33, p 5 |
| EP 911 020 | T 2, pp 11-12 |
| EP 916 335 | T 2-4, pp 19-41 |
| EP 924 246 | T 2, p 9 |
| EP 933 376 | Ex 1-15, pp 10-21 |
| EP 944 624 | Ex 1 + 2, pp 13-15 |
| EP 945 125 | T 3 a + b, pp 14-15 |
| EP 95 097 | Ex 1, p 4 |
| EP 967 200 | Ex 2; T 3-5, pp 17-20 |
| EP 969 004 | Ex 5, T 1, pp 6-8 |
| FR 2842806 A1 | Ex I p 10, Ex II p 12 |
| FR 2861075 A1 | Ex 1-3 on pp 12-14; |
| FR 2862641 | Formula 3 on p4; Ex A-J on pp 7-9; |
| FR 2869907 A1 | Formula 1 on p 6; T 1 on p 7-8; Ex 4-39 on pp 12-35; |
| KR 2004025954 | all kojyl benzoate derivatives |
| JP 06135985 A2 | Formula 1 on p 2; Ex 1-8 on pp 7-8; |
| JP 2000319629 | CAS Reg Nos. 80142-49-0, 137215-83-9, 307947-82-6 |
| JP 2003081910 A | Ex on p 1; |
| JP 2005289916 A | Formula I on p 1; Ex Ia-Id on pp 2-3; |
| JP 2005290240 A | Formulas I on p 2, Ex II on p 2; |
| US 2003/0053966A1 | Ex on pp 3-6 |
| US 2004057912 A1 | Ex on p 7-9, Ex 1 on p 10; |
| US 2004057914 A1 | Ex on p 8-12, Ex 1 on p 12; |
| US 2004/0057911A1 | Formula I and II on p 1; formula III and IV on p3; Ex 1-3 on pp 5-6; |
| US 2004/0071640A1 | Ex 1-12 on pp 4-7; |
| US 2004/0091433A1 | Ex 1-6 on pp 14-16; |
| US 2004/0136931A1 | Ex 1-3 on p 7; |
| US 2004/0258636A1 | Ex 1-11 on pp 9-15; |
| US 2005/0019278A1 | Ex 1-9 on pp 6-8; |
| US 2005/0136012A1 | Formula 1 on p 2; |
| US 2005/0136014A1 | Formula a-c on p 2; Examples on p 3; |
| US 2005/0201957A1 | Formula 1 on p1; Ex A, B, C, D, E, F, G on pp 2-3; |
| US 2005/0249681A1 | all compounds on pp 2-3, Ex 1 on p 6; |
| US 2005186157A1 | Formula 1 on p 1; Ex 1-6 on pp 2-4; |
| US 2005260144A1 | Formula I on p1; Formula II on p 3; Ex 1-10 on pp 8-11; |
| US 2006018848A1 | Ex a-p on pp 3-4; |
| US 2006045859A1 | Formula 1 on p 1; Ex 1-10 on pp 2-4; |
| U.S. Pat. No. 5,635,343 | all compounds on pp 5-10 |
| U.S. Pat. No. 5,332,568 | Ex 1, p 5, T 1 + 2, pp 6-8 |
| U.S. Pat. No. 5,338,539 | Ex 1-9, pp 3 + 4 |
| U.S. Pat. No. 5,346,691 | Ex 40, p 7; T 5, p 8 |

TABLE 2-continued

Suitable UV filter substances which can be additionally used with the UV absorbers according to the present invention

| | |
|---|---|
| U.S. Pat. No. 5,801,244 | Ex 1-5, pp 6-7 |
| U.S. Pat. No. 6,613,340 | Ex I, II pp 9-11, Examples on rows 28-53 p 6 |
| U.S. Pat. No. 6,800,274 B2 | Formulas I-VI and IX-XII on pp 14-18; |
| U.S. Pat. No. 6,890,520 B2 | Ex 1-10 on pp 6-9; |
| U.S. Pat. No. 6,926,887 B2 | Ex A on pp5/6; Formulas I-VIII on pp 27-29; |
| U.S. Pat. No. 6,936,735 B2 | Formulas 1-2 on p 2; formula 3-4 on p 6; |
| U.S. Pat. No. 6,962,692 B2 | Formulas VII and VIII on p 6; Formulas I, II, IV-VI, IX, X on pp 14-16; Formula III on p 19; |
| WO 0149686 | Ex 1-5, pp 16-21 |
| WO 0168047 | Tables on pp 85-96 |
| WO 0181297 | Ex 1-3, pp 9-11 |
| WO 0191695 | Formula I on p 4, T on p 8 |
| WO 0202501 A1 | Ex Ia-c, p 5 |
| WO 02069926 A1 | Ex on p 9, Ex on pp 17-23 |
| WO 02072583 | T on pp 68-70 |
| WO 02080876 | Ex 1 on pp 7-9 |
| WO 0238537 | All compounds p 3, compounds on rows 1-10 p 4 |
| WO 03004557 A1 | Ex A1-A29 on pp 36-57; |
| WO 03007906 | Ex I-XXIII, pp 42-48 |
| WO 03086341 A2 | Formula 2-21, pp 4-6; |
| WO 03092643 A1 | T on pp 34-35, compounds listed on p 16 |
| WO 03097577 A1 | Ex on pp 6-8; Ex 1-3 on pp 15-18; |
| WO 03104183 A1 | Formula I-IV on p 1; Ex 1-5 on pp 27-28; |
| WO 04000256 A1 | Ex 1-10 on pp 18-24 |
| WO 04020398 A1 | Ex 1-3 on pp 14-17 |
| WO 04020398 A1 | Formulas I-VI on pp 21-24, Formula IX on p 25; |
| WO 04075871 | Ex 1-3 on pp 17-18; Ex 7-9 on pp 21-22; |
| WO 05009938 A2 | Formula I on p 1; Ex 1-2 on pp 14-15; |
| WO 05065154 A2 | Formula a-c on pp 5-6; |
| WO 05080341 A1 | Formula 1 on p 3; Examples on pp 9-13; |
| WO 05107692 A1 | Formula 1 on p 2; Ex 1-9 on pp 27-29; |
| WO 05118562 A1 | Formula I on p 4; Ex Ia-Ig on p 5; |
| WO 05121108 A1 | Formula I on p 3; Formula Ia on p 5; T 1 on p 7; Ex 3-22 on pp 11-23; |
| WO 06009451 | T 1 on pp 5-8; Formulas III and UV0 on p 9; |
| WO 06016806 | T 1 on pp 6-7; T 2 on p 10; T 3 on p 11; T 4 on p 15; |
| WO 06032741 | Formulas 1-3 on p 1; Ex a-k on pp 5-7; Ex 1-4 on pp 18-20; |
| WO 9217461 | Ex 1-22, pp 10-20 |
| WO 9220690 | Polymeric Comp in Examples 3-6 |
| WO 9301164 | T 1 + 2, pp 13-22 |
| WO 9714680 | Ex 1-3, p 10 |

(Abbreviations T: Table, R: row, Comp: compound, Ex: compound(s) of Patent Example, p: page; the generic scope of the UV absorbers is described in the left-hand column; specific compounds are indicated in the right-hand column)

TABLE 3

Suitable UV filter substances and adjuvants which can be additionally used with the compounds of formula (1)

| No. | Chemical Name | CAS No. |
|---|---|---|
| 1 | (+/−)-1,7,7-trimethyl-3-[(4-methylphenyl)methylene]bicyclo[2.2.1]-heptan-2-one; p-methyl benzylidene camphor | 36861-47-9 |
| 2 | 1,7,7-trimethyl-3-(phenylmethylene)bicyclo[2.2.1]heptan-2-one; benzylidene camphor | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone | 131-57-7 |
| 7 | 2-Hydroxy-4-methoxy benzophenone-5-sulfonic acid | 4065-45-6 |
| 8 | 2,2'-dihydroxy-4,4'-dimethoxybenzophenone | 131-54-4 |
| 9 | 2,2'-Dihydroxy-4-methoxybenzophenone | 131-53-3 |
| 10 | Alpha-(2-oxoborn-3-ylidene)toluene-4-sulphonic acid and its salts; Mexoryl SL | 56039-58-8 |
| 11 | 1-[4-(1,1-dimethylethyl)phenyl]-3-(4-methoxyphenyl)propane-1,3-dione; avobenzone | 70356-09-1 |
| 12 | Methyl N,N,N-trimethyl-4-[(4,7,7-trimethyl-3-oxobicyclo[2,2,1]hept-2-ylidene)methyl]anilinium sulphate; Mexoryl SO | 52793-97-2 |
| 22 | 3,3,5-Trimethyl cyclohexyl-2-hydroxy benzoate; homosalate | 118-56-9 |
| 27 | Menthyl-o-aminobenzoate | 134-09-8 |
| 28 | Menthyl salicylate | 89-46-3 |
| 29 | 2-Ethylhexyl 2-cyano,3,3-diphenylacrylate; Octocrylene | 6197-30-4 |
| 30 | 2-ethylhexyl 4-(dimethylamino)benzoate | 21245-02-3 |
| 32 | 2-ethylhexyl salicylate | 118-60-5 |

TABLE 3-continued

Suitable UV filter substances and adjuvants which can be additionally used with the compounds of formula (1)

| No. | Chemical Name | CAS No. |
|---|---|---|
| 33 | Benzoic acid, 4,4',4''-(1,3,5-triazine-2,4,6-triyltriimino)tris-, tris(2-ethylhexyl)ester; 2,4,6-Trianilino-(p-carbo-2'-ethylhexyl-1'-oxi)-1,3,5-triazine; octyl triazone | 88122-99-0 |
| 34 | 4-aminobenzoic acid | 150-13-0 |
| 35 | Benzoic acid, 4-amino-, ethyl ester, polymer with oxirane | 113010-52-9 |
| 38 | 2-phenyl-1H-benzimidazole-5-sulphonic acid; phenylbenzimidazolsulfonic acid | 27503-81-7 |
| 39 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 40 | Triethanolamine salicylate | 2174-16-5 |
| 41 | 3,3'-(1,4-phenylenedimethylene)bis[7,7-dimethyl-2-oxo-bicyclo[2.2.1]heptane-1 methanesulfonic acid]; Cibafast H | 90457-82-2 |
| 42 | Titanium dioxide | 13463-67-7 |
| 44 | Zinc oxide | 1314-13-2 |
| 45 | 2,2'-Methylene-bis-[6-(2H-benzotriazol-2-yl)-4-(1,1,3,3-tetramethyl-butyl)-phenol]; Tinosorb M | 103597-45-1 |
| 46 | 2,4-bis{[4-(2-ethylhexyloxy)-2-hydroxy]-phenyl}-6-(4-methoxyphenyl)-(1,3,5)-triazine; Tinosorb S | 187393-00-6 |
| 47 | 1H-Benzimidazole-4,6-disulfonic acid, 2,2'-(1,4-phenylene)bis-, disodium salt | 180898-37-7 |
| 48 | Benzoic acid, 4,4'-[[6-[[4-[[(1,1-dimethylethyl)amino]carbonyl]phenyl]-amino]1,3,5-triazine-2,4-diyl]diimino]bis-, bis(2-ethylhexyl)ester; di-ethylhexyl butamido triazone; Uvasorb HEB | 154702-15-5 |
| 49 | Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane; Mexoryl XL | 155633-54-8 |
| 50 | Dimethicodiethylbenzalmalonate; Polysilicone 15; Parsol SLX | 207574-74-1 |
| 51 | Benzenesulfonic acid, 3-(2H-benzotriazol-2-yl)-4-hydroxy-5-(1-methylpropyl)-, monosodium salt; Tinogard HS | 92484-48-5 |
| 53 | 1-Dodecanaminium, N-[3-[[4-(dimethylamino)benzoyl]amino]propyl]-N,N-dimethyl-, salt with 4-methylbenzenesulfonic acid (1:1); Escalol HP610 | 156679-41-3 |
| 54 | 1-Propanaminium, N,N,N-trimethyl-3-[(1-oxo-3-phenyl-2-propenyl)-amino]-, chloride | 177190-98-6 |
| 55 | 1H-Benzimidazole-4,6-disulfonic acid, 2,2'-(1,4-phenylene)bis- | 170864-82-1 |
| 56 | 1,3,5-Triazine, 2,4,6-tris(4-methoxyphenyl)- | 7753-12-0 |
| 57 | 1,3,5-Triazine, 2,4,6-tris[4-[(2-ethylhexyl)oxy]phenyl]- | 208114-14-1 |
| 58 | 1-Propanaminium, 3-[[3-[3-(2H-benzotriazol-2-yl)-5-(1,1-dimethyl-ethyl)-4-hydroxyphenyl]-1-oxopropyl]amino]-N,N-diethyl-N-methyl-, methyl sulfate (salt) | 340964-15-0 |
| 59 | 2-Propenoic acid, 3-(1H-imidazol-4-yl)- | 104-98-3 |
| 60 | Benzoic acid, 2-hydroxy-, [4-(1-methylethyl)phenyl]methyl ester | 94134-93-7 |
| 61 | 1,2,3-Propanetriol, 1-(4-aminobenzoate); glyceryl PABA | 136-44-7 |
| 62 | Benzeneacetic acid, 3,4-dimethoxy-α-oxo- | 4732-70-1 |
| 63 | 2-Propenoic acid, 2-cyano-3,3-diphenyl-, ethyl ester | 5232-99-5 |
| 64 | Anthralinic acid, p-menth-3-yl ester | 134-09-8 |
| 65 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, |
| 66 | 1,3,5-Triazine-2,4,6-triamine, N,N'-bis[4-[5-(1,1-dimethylpropyl)-2-benzoxazolyl]phenyl]-N''-(2-ethylhexyl)- or Uvasorb K2A | 288254-16-0 |
| 68 | sterols (cholesterol, lanosterol, phytosterols), as described in WO0341675 | |
| 69 | mycosporines and/or mycosporine-like amino acids as described in WO2002039974, e.g. Helioguard 365 from Milbelle AG, isolated mycosporine like amino acids from the red alga porphyra umbilicalis (INCI: Porphyra Umbilicalis) that are encapsulated into liposomes,) | |
| 70 | alpha-lipoic-acid as described in DE 10229995 | |
| 71 | synthetic organic polymers as described in EP 1371358, [0033]-[0041] | |
| 72 | phyllosilicates as described in EP 1371357 [0034]-[0037] | |
| 73 | silica compounds as described in EP1371356, [0033]-[0041] | |
| 74 | inorganic particles as described in DE10138496 [0043]-[0055] | |
| 75 | latex particles as described in DE10138496 [0027]-[0040] | |
| 76 | 1H-Benzimidazole-4,6-disulfonic acid, 2,2'-(1,4-phenylene)bis-, disodium salt; Bisimidazylate; Neo Heliopan APC | 180898-37-7 |
| 77 | Pentanenitrile, 2-[2,3-dihydro-5-methoxy-3,3-dimethyl-6-[(2-methyl-2-propenyl)oxy]-1H-inden-1-ylidene]-4,4-dimethyl-3-oxo- | 425371-15-9 |
| 78 | Pentanenitrile, 2-(2,3-dihydro-6-hydroxy-5-methoxy-3,3-dimethyl-1H-inden-1-ylidene)-4,4-dimethyl-3-oxo- | 425371-14-8 |
| 79 | Benzenepropanenitrile, α-(2,3-dihydro-3,3,5-trimethyl-1H-inden-1-ylidene)-β-oxo- | 425371-11-5 |
| 80 | Cyclohexanepropanenitrile, α-[5-(1,1-dimethylethyl)-2,3-dihydro-3,3-dimethyl-1H-inden-1-ylidene]-1-methyl-β-oxo- | 425371-10-4 |
| 81 | Pentanenitrile, 2-[6-(acetyloxy)-2,3-dihydro-5-methoxy-3,3-dimethyl-1H-inden-1-ylidene]-4,4-dimethyl-3-oxo- | 425371-09-1 |

TABLE 3-continued

Suitable UV filter substances and adjuvants which can be additionally used with the compounds of formula (1)

| No. | Chemical Name | CAS No. |
|---|---|---|
| 82 | Pentanenitrile, 2-[2,3-dihydro-5-methoxy-3,3-dimethyl-6-[2-methyl-3-[1,3,3,3-tetramethyl-1-[(trimethylsilyl)oxy]disiloxanyl]propoxy]-1H-inden-1-ylidene]-4,4-dimethyl-3-oxo- | 425371-08-0 |
| 83 | Pentanenitrile, 2-(2,3-dihydro-5-methoxy-3,3,6-trimethyl-1H-inden-1-ylidene)-4,4-dimethyl-3-oxo- | 425371-07-9 |
| 84 | Pentanenitrile, 4,4-dimethyl-3-oxo-2-(2,3,7,8-tetrahydro-8,8-dimethyl-6H-indeno[5,6-b]-1,4-dioxin-6-ylidene)- | 425371-06-8 |
| 85 | Pentanenitrile, 2-(2,3-dihydro-3,3,6-trimethyl-1H-inden-1-ylidene)-4,4-dimethyl-3-oxo- | 425371-05-7 |
| 86 | Pentanenitrile, 2-(2,3-dihydro-3,3,5,6-tetramethyl-1H-inden-1-ylidene)-4,4-dimethyl-3-oxo- | 425371-04-6 |
| 87 | Pentanenitrile, 2-(2,3-dihydro-5-methoxy-3,3,4,6-tetramethyl-1H-inden-1-ylidene)-4,4-dimethyl-3-oxo- | 425371-03-5 |
| 88 | Pentanenitrile, 2-(2,3-dihydro-5,6-dimethoxy-3,3-dimethyl-1H-inden-1-ylidene)-4,4-dimethyl-3-oxo- | 261356-13-2 |

The compounds of formula (1) may also be used in admixture with hindered amine light stabilizers as disclosed in WO 03/103622, e,g, hindered nitroxyl, hydroxylamine and hydroxylamine salt compounds.

The compounds of formula (1) may also be used in admixture with phenolic antioxidants as disclosed in EP-A-1 126 811.

The compounds of formula (1) may also be used in admixture with merocyanine derivatives as disclosed in WO 07/014,848.

Personal Care Uses

The lactones of formula (1) may be used as single component or in mixture with other stabilizers in particular for skin-care products, bath and shower additives, preparations containing fragrances and odoriferous substances, hair-care products, dentifrices, deodorizing and antiperspirant preparations, decorative preparations, light protection formulations and preparations containing active ingredients.

Skin-care products are, in particular, body oils, body lotions, body gels, treatment creams, skin protection ointments, shaving preparations, such as shaving foams or gels, skin powders, such as baby powder, moisturizing gels, moisturizing sprays, revitalizing body sprays, cellulite gels and peeling preparations.

Suitable bath and shower additives are shower gels, bath-salts, bubble baths and soaps.

Preparations containing fragrances and odoriferous substances are in particular scents, perfumes, toilet waters and shaving lotions (aftershave preparations).

Suitable hair-care products are, for example, shampoos for humans and animals, in particular dogs, hair conditioners, products for styling and treating hair, perming agents, hair sprays and lacquers, hair gels, hair fixatives and hair dyeing or bleaching agents.

Suitable dentifrices are in particular tooth creams, toothpastes, mouth-washes, mouth rinses, anti-plaque preparations and cleaning agents for dentures.

Suitable decorative preparations are in particular lipsticks, nail varnishes, eye shadows, mascaras, dry and moist make-up, rouge, powders, depilatory agents and suntan lotions.

Suitable cosmetic formulations containing active ingredients are in particular hormone preparations, vitamin preparations, vegetable extract preparations and antibacterial preparations.

The mentioned body-care products may be in the form of creams, ointments, pastes, foams, gels, lotions, powders, make-ups, sprays, sticks or aerosols.

They preferably contain the stabilizers of formulae (1) and, optionally, other UV absorbers, sterically hindered amines, complexing agents and phenolic or non-phenolic antioxidants.

The present invention therefore also relates to a body-care product comprising at least one compound of formula (1).

The compounds o formula (1) are present in the body care and household products in a concentration of about 5 to about 10000 ppm, based on the total formulation, preferably from about 10 to about 5000 ppm, and most preferably from about 100 to about 1000 ppm.

The cosmetic compositions according to the present invention may also contain one or one more additional compounds as described below.

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of C12-C15 alcohols, acetylated lanolin alcohol, etc.

Esters of Fatty Acids

Esters of linear $C_6$-$C_{24}$ fatty acids with linear $C_3$-$C_{24}$ alcohols, esters of branched $C_6$-$C_{13}$carboxylic acids with linear C6-$C_{24}$ fatty alcohols, esters of linear $C_6$-$C_{24}$fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethyl-hexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropylmyristate, isopropylpalmitate, isopropylstearate, isopropyl isostearate, isopropyloleate, n-butylstearate, n-hexyllaurate, n-decyloleate, isooctylstearate, iso-nonylstearate, isononyl isononanoate, 2-ethylhexylpalmitate, 2-hexyllaurate, 2-hexyldecylstearate, 2-octyldodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Natural or Synthetic Triglycerides Including Glyceryl Esters and Derivatives

Di- or tri-glycerides, based on C6-C18 fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borago oil, etc.

Waxes

Including esters of long-chain acids and alcohols as well as compounds having wax-like properties, e.g., carnauba wax, beeswax (white or yellow), lanolin wax, candellila wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

Pearlescent Waxes

Ikylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially (aurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils

Mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Orqanosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Fluorinated or Perfluorinated Oils

Perfluorhexane, dimethylcyclohexane, ethylcyclopentane, polyperfluoromethylisopropyl ether.

Emulsifiers

Any conventionally usable emulsifier can be used for the compositions. Emulsifier systems may comprise for example: carbocyclic acids and their salts: alkaline soap of sodium, potassium and ammonium; metallic soap of calcium or magnesium; organic basis soap such as lauric, palmitic, stearic and oleic acid etc.; alkyl phosphates or phosphoric acid esters, acid phosphate, diethanolamine phosphate, potassium cetyl phosphate; ethoxylated carboxylic acids or polyethyleneglycol esters, PEG-n acylates; linear fatty alcohols having from 8 to 22 carbon atoms, branched from 2 to 30 mol of ethylene oxide and/or from 0 to 5 mol propylene oxide with fatty acids having from 12 to 22 carbon atoms and with alkylphenols having from 8 to 15 carbon atoms in the alkyl group; fatty alcohol polyglycolether such as laureth-n, ceteareth-n, steareth-n, oleth-n; fatty acid polyglycolether such as PEG-n stearate, PEG-n oleate, PEG-n cocoate; monoglycerides and polyol esters; C12-C22 fatty acid mono- and di-esters of addition products of from 1 to 30 mol of ethylene oxide with polyols; fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates; mixtures of compounds from a plurality of those substance classes are also suitable; fatty acid polyglycolesters such as monostearate diethylene glycol, fatty acid and polyethylene glycol esters, fatty acid and saccharose esters such as sucro esters, glycerol and saccharose esters such as sucro glycerides; sorbitol and sorbitan, sorbitan mono- and di-esters of saturated and unsaturated fatty acids having from 6 to 22 carbon atoms and ethylene oxide addition products; polysorbate-n series, sorbitan esters such as sesquiisostearate, sorbitan, PEG-(6)-isostearate sorbitan, PEG-(10)-sorbitan laurate, PEG-17-dioleate sorbitan, glucose derivatives, $C_8$-$C_{22}$ alkyl-mono and oligo-glycosides and ethoxylated analogues with glucose being preferred as the sugar component; O/W emulsifiers such as methyl gluceth-20 sesquistearate, sorbitan stearate/sucrose cocoate, methyl glucose sesquistearate, cetearyl alcohol/cetearyl glucoside; W/O emulsifiers such as methyl glucose dioleate/methyl glucose isostearate; sulfates and sulfonated derivatives, dialkylsulfosuccinates, dioctyl succinate, alkyl lauryl sulfonate, linear sulfonated parafins, sulfonated tetraproplyne sulfonate, sodium lauryl sulfates, amonium and ethanolamine lauryl sulfates, lauyl ether sulfates, sodium laureth sulfates, sulfosuccinates, aceyl isothionates, alkanolamide sulfates, taurines, methyl taurines, imidazole sulfates; amine derivatives, amine salts, ethoxylated amines, oxide amine with chains containing an heterocycle such as alkyl imidazolines, pyridine derivatives, isoquinoteines, cetyl pyridinium chlorure, cetyl pyridinium bromide, quaternary ammonium such as cetyltrimethylbroide amonium broide (CTBA), stearylalkonium. Amide derivatives, alkanolamides such as acylamide DEA, ethoxylated amides such as PEG-n acylamide, oxydeamide. Polysiloxane/polyalkyl/polyether copolymers and derivatives, dimethicone, copolyols, silicone polyethylene oxide copolymer, silicone glycol copolymer. Propoxylated or POE-n ethers (Meroxapols), Polaxamers or poly(oxyethylene)m-block-poly(oxypropylene)n-block(oxyethylene); zwitterionic surfactants that carry at least one quaternary ammonium group and at least one carboxylate and/or sulfonate group in the molecule; zwitterionic surfactants that are especially suitable are betaines, such as N-alkyl-N,N dimethylammonium glycinates, cocoalkyldimethylammonium glycinate, N-acylaminopropyl-N,N-dimethylammonium glycinates, cocoacylaminopropyldimethyl-ammonium glycinate and 2 alkyl-3-carboxymethyl-3-hydroxyethylimidazolines each having from 8 to 18 carbon atoms in the alkyl or acyl group and also cocoacylaminoethylhydroxy-ethylcarboxymethylglycinate, N-alkylbetaine, N-alkylaminobetaines; alkylimidazolines, alkylopeptides, lipoaminoacides, self emulsifying bases and the compounds as described in K. F. DePolo, A short textbook of cosmetology, Chapter 8, Table 8-7, p250-251.

Non ionic emulsifiers such as PEG-6 beeswax (and) PEG-6 stearate (and) polyglyceryl-2-isostearate [Apifac], glyceryl stearate (and) PEG-100 stearate; [Arlacel 165], PEG-5 glyceryl stearate [arlatone 983 S], sorbitan oleate (and) polyglyceryl-3 ricinoleate.[Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20[Polawax GP 200, Polawax NF], cetearyl alcohol and cetearyl polyglucoside [Emulgade PL 1618], cetearyl alcohol and ceteareth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and szareth-7 and steareth-10 [Emulsifying wax U.S.N.F], glyceryl stearate and PEG-75 stearate [Gelot 64], propylene glycol ceteth-3 acetate.[Hetester PCS], propylene glycol isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X].

Anionic emulsifiers such as PEG-2 stearate SE, glyceryl stearate SE [Monelgine, Cutina KD], propylene glycol stearate [Tegin P], cetearyl Alcohol and Sodium cetearyl sulfate [Lanette N, Cutina LE, Crodacol GP], cetearyl alcohol and sodium lauryl sulfate [Lanette W], trilaneth-4phosphate and glycol stearate and PEG-2 stearate [Sedefos 75], glyceryl stearate and sodium lauryl Sulfate [Teginacid Special]. Cationic acid bases such as cetearyl alcohol and cetrimonium bromide.

The emulsifiers may be used in an amount of, for example, from 1 to 30% by weight, especially from 4 to 20% by weight and preferably from 5 to 10% by weight, based on the total weight of the composition.

When formulated in O/W emulsions, the preferably amount of such emulsifier system could represent 5% to 20% of the oil phase.

Super-Fatting Agents

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Surfactants

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickeners and Rheology Modifiers

Silicon dioxide, magnesium silicates, aluminium silicates, polysaccharides or derivatives thereof for example hyaluronic acid, xanthan gum, guar-guar, agar-agar, alginates, carra-ghenan, gellan, pectines, or modified cellulose such as hydroxycellulose, hydroxypropylmethylcellulose. In addition polyacrylates or homopolymer of reticulated acrylic acids and polyacrylamides, carbomer (carbopol types 980, 981, 1382, ETD 2001, ETD2020, Ultrez 10) or Salcare range such as Salcare SC80 (steareth-10 alkyl ether/acrylates copolymer), Salcare SC81 (acrylates copolymer), Salcare SC91 and Salcare AST (sodium acrylates copolymer/PPG-1 trideceth-6), sepigel 305 (polyacrylamide/laureth-7), Simulgel NS and Simulgel EG (hydroxyethyl acrylate/sodium acryloyldimethyl taurate copolymer), Stabilen 30 (acrylates/vinyl isodecanoate crosspolymer), Pemulen TR-1 (acrylates/C10-30 alkyl acrylate crosspolymer), Luvigel EM (sodium acrylates copolymer), Aculyn 28 (acrylates/beheneth-25 methacrylate copolymer), etc.

Polymers

Suitable cationic polymers are, for example, cationic cellulose derivatives, for example a quaternised hydroxymethyl cellulose obtainable under the name Polymer JR 400 from Amerchol, cationic starches, copolymers of diallylammonium salts and acrylamides, quaternised vinylpyrrolidone/vinyl imidazole polymers, for example Luviquatâ (BASF), condensation products of polyglycols and amines, quaternised collagen polypeptides, for example lauryldimonium hydroxypropyl hydrolyzed collagen (LamequatâL/Grünau), quaternised wheat polypeptides, polyethyleneimine, cationic silicone polymers, for example amidomethicones, copolymers of adipic acid and dimethylaminohydroxypropyldiethylenetriamine (Cartaretin/Sandoz), copolymers of acrylic acid with dimethyldiallylammonium chloride (Merquat 550/Chemviron), polyaminopolyamides, as described, for example, in FR-A-2 252 840, and the crosslinked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example Jaguar C-17, Jaguar C-16 from Celanese, quaternised ammonium salt polymers, for example Mirapol A-15, Mirapol AD-1, Mirapol AZ-1 from Miranol. As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/methyl methacrylatetert. butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones. Furthermore the polymers as described in EP 1093796 (pages 3-8, paragraphs 17-68) may be used.

Cationic Surfactants cetyl trimethyl ammonium bromide (CTAB), dimethicone copolyols, amidomethicones, acrylamidopropyltrimonium chloride/Acrylamide copolymer, guar hydroxypropyl trimonium chloride, hydroxycetyl hydroxyethyl dimonium chloride quaternium compounds as listed in International Cosmetic Ingredient Dictionary and Handbook, 7$^{th}$ Edition 1997, for example Quaternium-80, polyquaternium compounds, as listed in International Cosmetic Ingredient Dictionary and Handbook, 7$^{th}$ Edition 1997, for example polyquaternium-5, polyquaternium-6, polyquaternium-7, polyquaternium-10, polyquaternium-11, polyquaternium-17, polyquaternium-18, polyquaternium-24 or polyquaternium-27, polyquaternium-28, polyquaternium-32, polyquaternium-37.

Biogenic Active Ingredients

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorising Active Ingredients

As deodorising active ingredients are for example, antiperspirants, for example aluminium chlorohydrates (see J. Soc. Cosm. Chem. 24, 281 (1973)). Under the trade mark Locronâ of Hoechst AG, Frankfurt (FRG), there is available commercially, for example, an aluminium chlorohydrate corresponding to formula Al2(OH)5Cl×2.5H2O, the use of which is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen CAT, Henkel), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Examples include chitosan, phenoxyethanol and chlorhexidine gluconate. 5-chloro-2-(2,4-dichlorophenoxy)phenol (Triclosan, Irgasan, Ciba Specialty Chemicals Inc.) has also proved especially effective.

Anti-Dandruff Agents

As anti-dandruff agents there may be used, for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Hydrotropic Agents

For improvement of the flow behaviour it is also possible to employ hydrotropic agents, for example ethoxylated or non ethoxylated mono-alcohols, diols or polyols with a low number of carbon atoms or their ethers (e.g. ethanol, isopropanol, 1,2-dipropanediol, propyleneglycol, glycerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols for that purpose comprise preferably 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives

Suitable preservatives include, for example methyl-, ethyl-, propyl-, butyl-parabens, benzalkonium chloride, 2-bromo-2-nitro-propane-1,3-diol, dehydroacetic acid, diazolidinyl urea, 2-dichloro-benzyl alcohol, dmdm hydantoin, formaldehyde solution, methyldibromoglutanitrile, phenoxyethanol, sodium hydroxymethylglycinate, imidazolidinyl urea, triclosan and further substance classes listed in the following reference: K. F. Depolo—A Short Textbook Of Cosmetology, Chapter 7, Table 7-2, 7-3, 7-4 And 7-5, P210-219.

Bacteria-Inhibiting Agents

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

Perfume Oils

Mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Other Adjuvants

It is furthermore possible for the cosmetic preparations to contain, as adjuvants, anti-foams, such as silicones, structurants, such as maleic acid, solubilisers, such as ethylene glycol, propylene glycol, glycerol or diethylene glycol, opacifiers, such as latex, styrene/PVP or styrene/acrylamide copolymers, propellants, such as propane/butane mixtures, N2O, dimethyl ether, CO2, N2 or air, so-called coupler and developer components as oxidation dye precursors, reducing agents, such as thioglycolic acid and derivatives thereof, thiolactic acid, cysteamine, thiomalic acid or mercaptoethanesulfonic acid, or oxidising agents, such as hydrogen peroxide, potassium bromate or sodium bromate.

Suitable insect repellents are, for example, N,N-diethyl-m-toluamide, 1,2-pentanediol or insect repellent 3535; suitable self-tanning agents are, for example, dihydroxyacetone and/or erythrulose or dihydroxy acetone and/or dihydroxy acetone precursors as described in WO 01/85124 and/or erythrulose.

The present stabilizer systems are particularly suitable for stabilizing body care products, in particular:

skin-care preparations, e.g. skin-washing and cleansing preparations in the form of tablet-form or liquid soaps, soapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils; body oils, body lotions, body gels; skin protection ointments;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances and odoriferous substances containing preparations (scents, eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile;

dentifrices, in particular tooth creams, toothpastes, mouthwashes, mouth rinses, anti-plaque preparations and cleaning agents for dentures;

decorative preparations, in particular lipsticks, nail varnishes, eye shadows, mascaras, dry and moist make-up, rouge, powders, depilatory agents and suntan lotions cosmetic formulations containing active ingredients, in particular hormone preparations, vitamin preparations, vegetable extract preparations and antibacterial preparations.

Suitable cosmetic formulations containing active ingredients are in particular hormone preparations, vitamin preparations, vegetable extract preparations and antibacterial preparations.

Presentation Forms

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion,
in the form of a stick,
in the form of a spray (spray with propellent gas or pump-action spray) or an aerosol,
in the form of a foam, or
in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition:
0.01 to 5% by weight of the compound of formula (1),
12.0% by weight of sodium laureth-2-sulfate,
4.0% by weight of cocamidopropyl betaine,
3.0% by weight of sodium chloride,
and water ad 100%.

For example, especially the following hair-cosmetic formulations may be used:
a1) spontaneously emulsifying stock formulation, comprising the compound of formula (1) according to the invention, optionally another stabilizer, PEG-6-C10oxoalcohol and sorbitan sesquioleate, to which water and any desired quaternary ammonium compound, for example 4% minkamidopropyl dimethyl-2-hydroxyethylammonium chloride or Quaternium 80 is added;
a2) spontaneously emulsifying stock formulation comprising the compound of formula (1) according to the invention, optionally another stabilizer, tributyl citrate and PEG-20-sorbitan monooleate, to which water and any desired quaternary ammonium compound, for example 4% minkamidopropyl dimethyl-2-hydroxyethylammonium chloride or Quaternium 80 is added;
b) quat-doped solutions comprising the compound of formula (1) according to the invention in butyl triglycol and tributyl citrate; and optionally another stabilizer;
c) mixtures or solutions comprising the compound of formula (1) according to the invention with alkylpyrrolidone; and optionally another stabilizer.

Examples of body care products of the present invention are listed in the Table below:

| Body care product | Ingredients |
| --- | --- |
| moisturising cream | vegetable oil, emulsifier, thickener, perfume, water, stabilizer of formula (1), UV absorbers |
| shampoo | surfactant, emulsifier, preservatives, perfume, stabilizer of formula (1), UV absorbers |
| Toothpaste | cleaning agent, thickener, sweetener, flavor, colorant, stabilizer of formula (1), water, UV absorbers |
| lip-care stick | vegetable oil, wax, $TiO_2$, stabilizer of formula (1), UV absorbers |

Household Products

The stabilizer systems of the present invention are also used in household cleaning and treatment agents, for example in laundry products and fabric softeners, liquid cleansing and scouring agents, glass detergents, neutral cleaners (all-purpose cleaners), acid household cleaners (bath), bathroom cleaners, WC cleaners, for instance in washing, rinsing and dishwashing agents, kitchen and oven cleaners, clear rinsing agents, dishwasher detergents, shoe polishes, polishing waxes, floor detergents and polishes, metal, glass and ceramic cleaners, textile-care products, rug cleaners and carpet shampoos, agents for removing rust, color and stains (stain remover salt), furniture and multipurpose polishes and leather and vinyl dressing agents (leather and vinyl sprays) and air fresheners.

Household cleaning agents are aqueous or alcoholic (ethanol or isopropyl alcohol) solutions of one or more of the following components:
 anionic, nonionic, amphoteric and/or cationic surfactants
 soaps, prepared by saponification of animal and vegetable greases
 organic acids, like hydrochloric acid, phosphoric acid, or sulfuric acid,
 for basic products inorganic (NaOH or KOH) or organic bases;
 abrasives for improved cleaning of surfaces,
 waxes and/or silicones for maintenance and protection of surfaces,
 polyphosphates,
 substances which eliminate hypochlorite or halogens;
 peroxides comprising bleaching activators like TAED, for example sodium perborate or $H_2O_2$;
 enzymes;
 in washing detergents discoloration inhibitors, soil-release compounds, grey scale inhibitors, foam inhibitors, fluorescent whitening agents;
 cleaning agents based on wax may comprise solvents selected from benzine, turpentine and/or paraffines and emulsifiers based on wax;
 filling agents like silicates, polyphosphates, Zeolithes for powdery cleaning agents;
 pigments, lakes or soluble dyes;
 perfumes; and
 light stabilizers, antioxidants and chelating agents.

Colored cleaning agents and decorative cosmetic products can comprise the following dyes:
 inorganic pigments, for example iron oxide (Iron Oxide Red, Iron Oxide Yellow, Iron Oxide Black, etc.), Ultramarines, Chromium Oxide Green or Carbon Black;
 natural or synthetic organic pigments;
 disperse dyes which may be solubilzed in solvents like direct hair dyes of the HC type, for example HC Red No. 3, HC Blue No. 2 and all other hair dyes listed in International Cosmetic Ingredient Dictionary and Handbook, 7th edition 19997) or the dispersion dyes listed in Color Index International or Society of Dyers and Colourists;
 color varnishes (insoluble salts of soluble dyes, like many Ca-, Ba- or Al-salts of anionic dyes);
 soluble anionic or cationic dyes, like acid dyes (anionic), basic dyes (cationic), direct dyes, reactive dyes or solvent dyes.

Generally, for the coloration of household- and body care products all substances are suitable which have an absorption in the visible light of electromagnetic radiation (wave length of ca. 4000 to 700 nm). The absorption is often caused by the following chromophores: Azo- (mono-, di, tris-, or poly-) stilbene-, carotenoide-, diarylmethan-, triarylmethan-, xanthen-, acridin-, quinoline, methin- (also polymethin-), thiazol-, indamin-, indophenol-, azin-, oxazin, thiazin-, anthraquinone-, indigoid-, phtalocyanine- and further synthetic, natural and/or inorganic chromophores.

The present invention also relates to home care and fabric care products such as drain cleaners, disinfectant solutions, upholstery cleaners, automotive care products (e.g., to clean and/or polish and protect paint, tires, chrome, vinyl, leather, fabric, rubber, plastic and fabric), degreasers, polishes (glass, wood, leather, plastic, marble, granite, and tile, etc.), and metal polishes and cleaners. Antioxidants are suitable to protect fragrances in above products as well as in dryer sheets. The present invention also relates to home care products such as candles, gel candles, air fresheners and fragrance oils (for the home).

Typical examples of household cleaning and treating agents are listed in the table below:

| Household cleaners/household treating agents | Ingredients |
| --- | --- |
| detergent concentrate | surfactant mixture, ethanol, stabilizer of formula (1), water, UV absorbers, other antioxidants |
| shoe polishwax | wax emulsifier, antioxidant, water, preservative, UV absorbers, stabilizer of formula (1) |
| wax-containing floor cleaning agent | emulsifier, wax, sodium chloride, stabilizer of formula (1), water, preservative UV absorbers, other antioxidants |

The stabilizers of formula (1) according to the present invention are for example incorporated by dissolution in an oil phase or alcoholic or water phase, where required at elevated temperature.

The present body care products and household products have high stability towards color changes and chemical degradation of the ingredients present in these products. For example, present compositions that comprise a dye are found to have excellent color stability.

The following Examples illustrate the invention.

A. ANTIOXIDATION TEST EXAMPLES

Example A1

Stabilizer 1

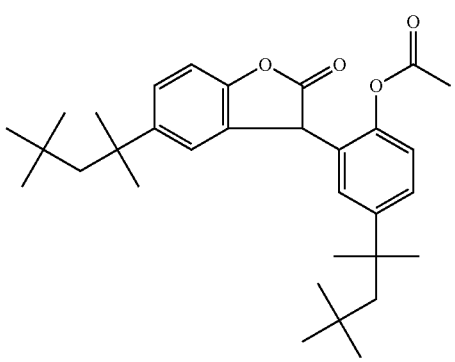 [SMILES: CC(=O)Oc1ccc(C(C)(C)CC(C)(C)C)cc1C1C(=O)Oc2ccc(C(C)(C)CC(C)(C)C)cc21]

The following stabilized and unstabilized samples were prepared for antioxidation testing:

Sample 1: Peach Kernel Oil
Sample 2: Peach Kernel Oil additionally containing 0.05% of Stabilizer 1

The samples are placed in a RANCIMAT and heated to 100° C. An airflow of 15 L/min is adjusted. The airstream bubbles are conducted through each heated sample and afterwards through a water reservoir. Thus all volatile organic compounds formed by the oxidation process are carried into the water reservoir by the airstream. The conductivity of the water reservoir is monitored online during the measurement. Once oxidation starts volatile organic compounds like formic acid are transported into the water reservoir which results in a rapid (exponential) increase of conductivity. The time until oxidation starts is called "induction time".

The results are listed in the table below.

| Sample | Induction Time |
| --- | --- |
| 1 | 2.3 |
| 2 | 3.8 |

Sample 2 comprising a stabilizer according to the present invention exhibits a significant longer induction time and therefore a better oxidation stability compared to the unstabilized sample.

Example A2

The following stabilized and unstabilized samples were prepared for antioxidation testing:

| Sample | Induction Time |
| --- | --- |
| Sample 1 | Evening Primrose Oil |
| Sample 2 | Evening Primrose Oil additionally containing 0.05% of Stabilizer 1 |
| Sample 3 | Evening Primrose Oil additionally containing 0.05% of Octadecyl Di-t- butyl-4-hydroxyhydrocinnamate |
| Sample 4 | Evening Primrose Oil additionally containing 0.05% of Tetrabutyl Ethylidinebisphenol |

The samples are placed in a RANCIMAT and heated to 100° C. An airflow of 15 L/min is adjusted. The airstream bubbles are conducted through each heated sample and afterwards through a water reservoir. Thus all volatile organic compounds formed by the oxidation process are carried into the water reservoir by the airstream. The conductivity of the water reservoir is monitored online during the measurement. Once oxidation starts volatile organic compounds like formic acid are transported into the water reservoir which results in a rapid (exponential) increase of conductivity. The time until oxidation starts is called "induction time".

The results are listed in the table below.

| Sample | Induction Time |
| --- | --- |
| Sample 1 | 2.4 |
| Sample 2 | 3.7 |
| Sample 3 | 3.4 |
| Sample 4 | 3.6 |

Sample 2 comprising a stabilizer according to the present invention exhibits better oxidation stability compared to the unstabilized sample and compared to State of the art phenolic antioxidants like Octadecyl Di-t-butyl-4-hydroxyhydrocinnamate (Sample 3) and Tetrabutyl Ethylidinebisphenol (Sample 4).

Example A3

Formulations composed of a 80:20 alcohol-water mixture and 10% of various fragrances is stored at 40° C. for 1 month, each unstabilized, stabilized with BHT and stabilized with stabilizer 1. After storage the samples are observed for color changes and freshness (fragrance intensity/changes).

It was found that unstabilized samples, and some of the samples containing BHT, tended to discolor (yellowing) upon storage, while products stabilized with stabilizer 1 did not discolor and exhibited the overall best olfactory performance.

Results are especially favorable for stabilizer 1 when the fragrances contain vanillin.

B. APPLICATION EXAMPLES

Preparation of Body-Care and Household Formulations

| Phase | Ingredients | (w/w) % |
|---|---|---|
| A | carbomer (1% dispersion) | 0.30 |
|   | water, demin. | 30.00 |
| B | glycerol | 2.00 |
|   | methylparaben | 0.20 |
| C | water, demin. | ad 100 |
|   | PVP/VA copolymer | 8.00 |
|   | triethanolamine (88%) | 0.12 |
|   | EDTA, disodium salt | 0.01 |
|   | stabilizer 1 | 0.10 |

Preparation:

The components (A) are dispersed at room temperature.

(B) is mixed under heating until the paraben is completely dissolved and then (B) is added with gentle stirring to (A).

(C) is blended until it is completely dissolved and is slowly added under stirring to the mixture of (A) and (B).

The transparency of the gel can be increased by adding small amounts of triethanolamine (pH=5.6-5.75).

| Ingredients | (w/w) % |
|---|---|
| cocoamidopropylbetaine | 35.00 |
| water, demin. | ad.100 |
| citric acid | q.s. (pH) |
| polyquaternium-15 | 0.15 |
| perfume oil | 0.30 |
| chlorophyll | 0.20 |
| TINOGARD HS | 0.02 |
| stabilizer 1 | 0.02 |
| colorant (D&C Yellow No. 5) | 0.02 |
| sodium chloride | 0.30 |

Preparation: Surfactant and water are blended until a homogeneous solution is obtained. The pH is adjusted to 6.0-6.5 with citric acid and the other components are added in the indicated sequence. The mixture is stirred until it is completely dissolved.

Example B3

Preparation of a Perfume

| Ingredients | (w/w) % |
|---|---|
| ethanol, 96% | 60 |
| d-limonene | 5 |
| cedrene | 1.5 |
| citronellol | 0.5 |
| vanillin | 0.5 |
| Benzotriazolyl Dodecyl p-Cresol | 0.05 |
| Tris (Tetramethylhydroxypiperidinol) Citrate | 0.05 |
| Pentaerythrityl Tetra-di-t-butyl Hydroxyhydrocinnamate | 0.03 |
| stabilizer 1 | 0.02 |
| EDTA, Sodium Salt | 0.01 |
| colorant (D&C Yellow No. 5) | 0.1 |
| water | ad. 100 |

Preparation: The components are thoroughly mixed in the indicated sequence at 50° C. A clear homogeneous solution is obtained.

Example B4

Preparation of a Green-Colored Glass Detergent

| Ingredients | (w/w) % |
|---|---|
| anionic/amphoteric surfactants (Lumorol RK) | 0.7 |
| butyl glycol | 5.0 |
| isopropanol | 20.0 |
| d-limonene | 4.00 |
| colorant (D&C Green No. 2) | 0.05 |
| Sodium Benzotriazolyl Butylphenol Sulfonate | 0.10 |
| stabilizer 1 | 0.05 |
| water, demin. | ad. 100 |

Preparation: The components are dissolved in the indicated sequence until a clear homogeneous mixture is obtained.

Example B5

Preparation of a Floor Wax

| Ingredients | (w/w) % |
|---|---|
| wax mixture | 12 |
| white spirit | ad 100 |
| fragrance | 1.00 |
| stabilizer 1 | 0.10 |

Preparation: The components are stirred in the indicated sequence until a homogeneous mixture is obtained.

Example B6

Preparation of a Leather Cleaning Agent

The stabilizer is predissolved in the terpene. The components are then stirred in the cited sequence at about 65° C. until homogeneous. The mixture is then cooled to room temperature.

| Ingredients | (w/w) % |
|---|---|
| synthetic soap (Zetesap 813) | 7.85 |
| Glycerol | 6.00 |
| anionic surfactant (Lumorol 4192; Mulsifan RT 13) | 22.00 |
| Vaseline | 11.00 |
| paraffin 52/54 | 20.00 |
| Talcum | 2.00 |
| orange terpene | 4.00 |
| Stabilizer 1 | 0.05 |
| Water | 27.13 |

Excellent results are achieved for this example of a leather dressing and cleaning agent composition. Upon storage at 40° C. for 1 month the formulation performance is better than the same formulation stabilized with state-of-the-art phenolic antioxidant BHT.

| Ingredients | (w/w) % |
|---|---|
| Carnauba wax | 2.5 |
| Beeswax, white | 20.0 |
| Ozekerite | 10.0 |
| Lanoline, anhydrous | 5.0 |
| Cetyl alcohol | 2.0 |
| Liquid paraffin | 3.0 |
| Isopropyl Myristate | 3.0 |
| Propylene glycol recinoleate | 4.0 |
| CI Pigment Red 4 | 9.0 |
| CI Pigment Blue 15 | 1.0 |
| stabilizer 1 | 0.1 |
| Bis-Ethylhexyloxyphenol Methoxyphenyl Triazine | 1.0 |
| Castor Oil | ad 100 |

| Ingredients | (w/w) % |
|---|---|
| Cyclomethicone | 41.50 |
| Isodecane | 10.00 |
| D&C Red No. 7 Ca Lake | 8.00 |
| Synthetic wax | 6.00 |
| Isostearyltrimethylpropane siloxysilicate | 5.00 |
| Cetylstearate/acetylated lanolin, 90:10 | 5.00 |
| Ceresin | 4.00 |
| Paraffin | 3.00 |
| Titanium dioxide | 2.00 |
| Methylparaben | 0.30 |
| Propylparaben | 0.10 |
| stabilizer 1 | 0.10 |
| Bumetrizole | 0.10 |

| Ingredients | (w/w) % |
|---|---|
| Talcum | 56 |
| Zinc Stearate | 15 |
| Rice starch | 15 |
| Iron Oxide Red | 12 |
| Perfume | q.s. |
| stabilizer 1 | 0.1 |

| Ingredients | (w/w) % |
|---|---|
| Titanium dioxide | 12.79 |
| Oleyl alcohol | 4.57 |
| Glyceryl stearate | 3.65 |
| Propylene glycol | 3.65 |
| Stearic acid | 1.83 |
| Magnesium aluminium silicate | 0.91 |
| Triethanolamine 99% | 0.91 |
| Iron Oxide Yellow | 0.64 |
| Iron Oxide Red | 0.32 |
| CI Pigment Brown 6 | 0.37 |
| Carboxymethyl cellulose | 0.10 |
| stabilizer 1 | 0.02 |
| Pentaerythrityl Tetra-di-t-butyl Hydroxyhydrocinnamate | 0.02 |
| Water | ad 100 |

| Ingredients | (w/w) % |
|---|---|
| Polysaccharide resin (Kama KM 13, Kama) | 8.00 |
| Iron Oxide Black | 6.50 |
| Carnauba wax | 1.00 |
| Polysaccharide resin (Kama KM 13, Kama) | 8.00 |
| Triethanolamin, 99% | 1.00 |
| Hydrogenated polyisobutane | 1.00 |
| Hydrogenated polydecene | 1.00 |
| Sorbitan sesquioleate | 1.00 |
| Xanthum gum | 0.50 |
| Carboxymethyl cellulose | 0.40 |
| Magnesium aluminium silicate | 0.40 |
| Methyl paraben | 0.35 |
| Stearic acid | 2.50 |
| Lecithin | 0.20 |
| Imidazolidinyl urea | 0.10 |
| Benzotriazolyl Dodecyl p-Cresol | 0.10 |
| stabilizer 1 | 0.05 |
| Water | to 100 |

| Ingredients | (w/w) % |
|---|---|
| Paraffin Wax | 10.00 |
| Starch | 5.00 |
| Polyethylene | 5.00 |
| Iron Oxide Black | 7.00 |
| Carbomer (Carbopol, BFGoodrich) | 0.50 |
| Hydroxyethylcellulose | 0.50 |
| Panthenol | 2.00 |
| stabilizer 1 | 0.05 |
| Water | ad 100 |

| Ingredients | (w/w) % |
|---|---|
| Poly(1-trimethylsilyl propylene) | 0.30 |
| Nitrocellulose | 12.00 |
| Alkyd resin | 10.00 |
| Dibutyl phthalate | 4.00 |
| Camphor | 2.00 |
| Butyl acetate | 49.50 |
| Toluene | 20.00 |
| Pigment Red 57.1 | 1.00 |
| Quaternary bentonite | 1.00 |
| Bumetrizole | 0.50 |
| stabilizer 1 | 0.10 |

| Ingredients | (w/w) % |
| --- | --- |
| sodium laureth sulfate (30%, TEXAPON NSO, Cognis) | 30% |
| cocamidopropylbetaine (30%, DEHYTON K, Cognis) | 10% |
| colorant* | 0.001% |
| stabilizer 1 | 0.05% |
| Benzophenone-4 | 0.10% |
| Fragrance containing vanillin & Indol | 0.50% |
| citric acid (10% aqueous solution) | to pH 6 |
| deionized water | to 100% |

*Colorant is PURICOLOR BLUE ABL9 (FD&C Blue No. 1)

Example B15

Emulsion with Natural Oil

| Phase | Ingredients | (w/w) % |
| --- | --- | --- |
| A | passionflower oil | 8 |
|   | glyceryl dioleate | 4 |
|   | dicapryl ether | 4 |
|   | Isopropylisostearate | 4 |
|   | Stabilizer 1 | 0.05 |
| B | water, demin. | ad. 100 |
|   | EDTA | 0.1 |
| C | Carbomer | 0.15 |
| D | sodium hydroxide | 10% |
|   |   | 0.20 |
| E | perfume; preservative | q.s. |

The components of phase A are thoroughly mixed in a homogenizer for 10 min at 75-80° C. The water phase B, likewise heated to 75-80° C. beforehand, is slowly added and the mixture is homogenized for 1 min. The mixture is cooled, with stirring, to 40° C. and then phases C and E are added and the mixture is homogenized for 1 min. Subsequently, phase D is added and the mixture is homogenized for ½ min and cooled, with stirring, to room temperature. The formulation with and without the instant stabilizer are stored at 40° C. for 1 months.

By means of visual and olfactory assessment it is seen that the stabilizer of the present invention provide excellent color stability in personal care products.

Example B16

Stabilization of Hydroquinone (Active for Skin Whitening Cream)

| Phase | INCI Name | Trade Name | Supplier | Parts |
| --- | --- | --- | --- | --- |
| A | Self-emulsifying wax | N/A | N/A | 4.00 |
| A | Cetyl Alcohol | Lanette 16 | Cognis | 1.00 |
| A | Glyceryl Stearate | Tegin 4100 | Degussa | 2.50 |
| B | Glycerin | N/A | Merck | 3.00 |
| B | Deionized Water | Deionized Water | N/A | Qs to 100% |
| C | Sodium Acrylates Copolymer and Paraffinium Liquidum (and) PPG-1 Trideceth-6 | Salcare SC 91 | Ciba | 3.00 |
| D | Alcohol | N/A | N/A | 30.00 |
| D | Hydroquinone | N/A | Eastman | 5.00 |
| E | Fragrance | Fragrance | N/A | qs |
| E | DMDM Hydantoin | Nipa DMDMH | Nipa | qs |

We took the formulation, added various state-of-the-art stabilizers at 0.2% to phase D and stored the samples at 40° C. for four weeks. The results were compared to a stabilizer according to present invention. We found that some discoloration was visible even with state-of-the-art phenolic antioxidants like BHT or TINOGARD TS (Octadecyl Di-t-butyl-4-hydroxyhydrocinnamate). However, surprisingly the stabilizer 1 according to current invention was most effective and no discoloration was observed after storage.

| Ingredients | (w/w) % |
| --- | --- |
| DME (Propellant) | 30 |
| Polymeric emulsifier | 18 |
| Disodium EDTA | 0.05 |
| Pluronic 10R5 (surfactant) | 1 |
| Triethanolamine | 0.3 |
| Goodrite K752 (Acrylate Polymer) Goodrite 752 | 0.3 |
| Stablizer 1 | 0.02 |
| Benzotriazolyl Dodecyl p-Cresol | 0.05 |
| Water | to 100 |

The invention claimed is:

1. A method for protecting body-care and household products from photolytic and oxidative degradation by adding thereto stabilizers of formula

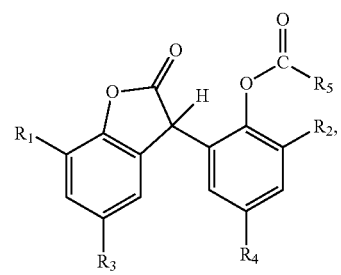

(1)

wherein
$R_1$ and $R_2$ are each independently of one another hydrogen; or $C_1$-$C_8$alkyl;
$R_3$ and $R_4$ are each independently of one another $C_1$-$C_{12}$alkyl; and
$R_5$ is $C_1$-$C_7$alkyl.

2. The method according to claim 1, wherein
$R_1$ and $R_2$ are each independently of one another hydrogen; or $C_1$-$C_4$alkyl;
$R_3$ and $R_4$ are each independently of one another $C_4$-$C_{10}$alkyl, and
$R_5$ is $C_1$-$C_4$alkyl.

3. The method according to claim 1, wherein
$R_3$ and $R_4$ are tert-octyl.

4. The method according to claim 1, wherein
$R_1$ and $R_2$ are hydrogen,
$R_3$ and $R_4$ are tert-octyl, and
$R_5$ is methyl.

5. The method according to claim 1 in body-care products for the skin and its adnexa.

6. The method according to claim 5, wherein the body-care products are selected from skin-care products, bath and shower additives, preparations containing fragrances and odoriferous substances, hair-care products, dentifrices, deodorizing and antiperspirant preparations, decorative preparations, light protection formulations and preparations containing active ingredients.

7. The method according to claim 5, wherein the body-care products are selected from body oils, body lotions, body gels, treatment creams, skin protection ointments, shaving preparations and skin powders.

8. The method according to claim 5, wherein the body-care products contain fragrances and odoriferous substances which are selected from scents, perfumes, toilet waters, shaving lotions and aftershave preparations.

9. The method according to claim 5, wherein the body-care products are hair-care products and are selected from shampoos, hair conditioners, products for styling and treating hair, perming agents, hair sprays and lacquers, hair gels, hair fixatives and hair dyeing or bleaching agents.

10. The method according to claim 5, wherein the body-care products are decorative preparations and are selected from lipsticks, nail varnishes, eye shadows, mascaras, dry and moist make-up, rouge, powders, depilatory agents and suntan lotions.

11. The method according to claim 5, wherein the body-care products contain active ingredients and are selected from hormone preparations, vitamin preparations, vegetable extract preparations and antibacterial preparations.

12. The method according to claim 1 wherein the household product is a household cleaning and treating agent.

13. The method according to claim 12 wherein the household cleaning and treating agents are selected from washing, rinsing and dishwashing agents, shoe polishes, polishing waxes, floor detergents and polishes, all purpose cleaners, bath and toilet cleaners, kitchen cleaners, car shampoos and waxes, neutral, acidic and alkaline cleaners, metal, glass and ceramic cleaners, textile care agents, agents for removing rust, color and stains (stain remover salt), bleaches, furniture and multipurpose polishes, surface protecting formulations, film forming formulations, air care formulations and candles.

14. A body-care product, which comprises at least one stabilizer according to claim 1.

15. A household cleaning and treating agent, which comprises at least one stabilizer according to claim 1.

* * * * *